United States Patent
Austerlitz et al.

(10) Patent No.: US 7,574,894 B2
(45) Date of Patent: Aug. 18, 2009

(54) ASM OUTPUT ULTRASONIC OXYGEN SENSOR

(75) Inventors: Howard Austerlitz, Stony Brook, NY (US); Lenard Hirshman, Freeport, NY (US); Ronald Bueter, Cary, NC (US); Stan Wood, Bushkill, PA (US)

(73) Assignee: Parker-Hannifin Corporation, Cleveland, OH (US)

( * ) Notice: Subject to any disclaimer, the term of this patent is extended or adjusted under 35 U.S.C. 154(b) by 349 days.

(21) Appl. No.: 11/380,114

(22) Filed: Apr. 25, 2006

(65) Prior Publication Data

US 2007/0245802 A1   Oct. 25, 2007

(51) Int. Cl.
*G01N 29/02* (2006.01)
(52) U.S. Cl. .................. 73/24.01; 73/24.06; 73/597
(58) Field of Classification Search .............. 73/1.82, 73/24.01, 24.06, 597
See application file for complete search history.

(56) References Cited

U.S. PATENT DOCUMENTS

| | | | |
|---|---|---|---|
| 5,060,514 A | 10/1991 | Aylsworth | |
| 5,627,323 A | 5/1997 | Stern | |
| 5,746,806 A | 5/1998 | Aylsworth et al. | |
| 6,418,782 B1 | 7/2002 | Sato et al. | |
| 6,491,739 B1 | 12/2002 | Crome et al. | |
| 6,547,188 B2 | 4/2003 | Schmutz et al. | |
| 6,634,598 B2 | 10/2003 | Susko | |
| 6,739,359 B2 | 5/2004 | Jones et al. | |
| 6,823,716 B2 | 11/2004 | Kelner et al. | |
| 2002/0062681 A1* | 5/2002 | Livingston | 73/24.01 |
| 2003/0136193 A1 | 7/2003 | Fujimoto | |

OTHER PUBLICATIONS

Written Opinion for International Application No. PCT/US2007/067394 dated Mar. 5, 2008.

* cited by examiner

*Primary Examiner*—Daniel S Larkin
(74) *Attorney, Agent, or Firm*—Renner, Otto, Boisselle & Sklar, LLP

(57) ABSTRACT

A gas measuring method, apparatus and system for measuring a concentration of a gas of interest is disclosed. The gas concentration is based on a propagation delay of a sonic or ultrasonic wave as the wave travels through the gas. The propagation delay is measured such that delay contributions from sources other than the gas itself are canceled. A sensor in accordance with the invention includes an sonic or ultrasonic transmitter and receiver, and a control module for performing calculations. The sensor can be used in various applications, including on-board inert gas generating systems (OBIGGS).

18 Claims, 6 Drawing Sheets

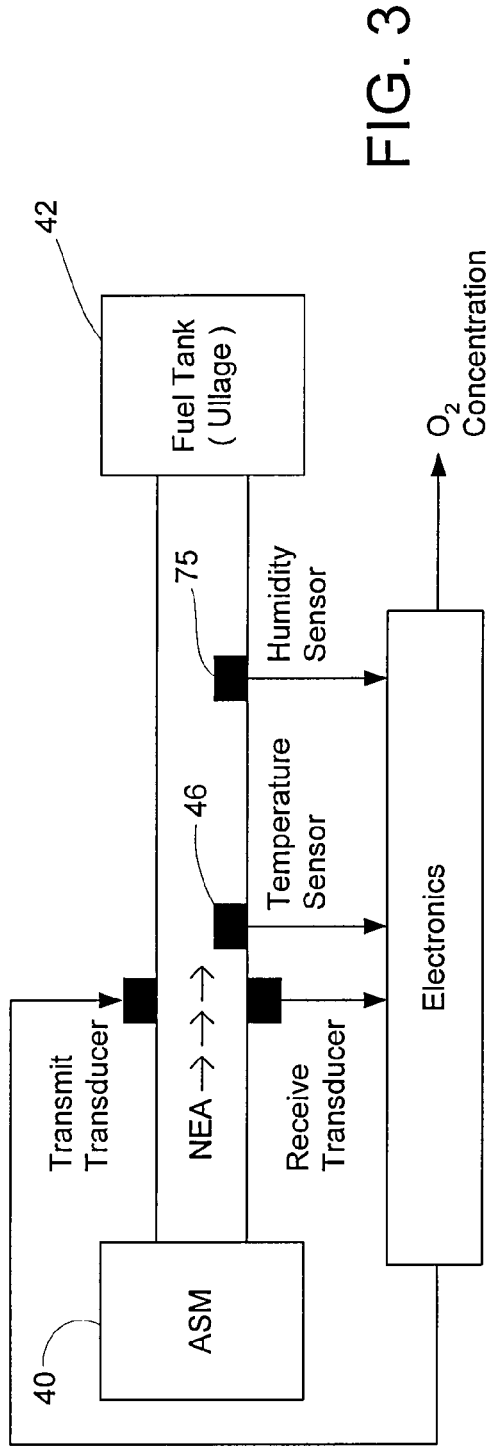
FIG. 3
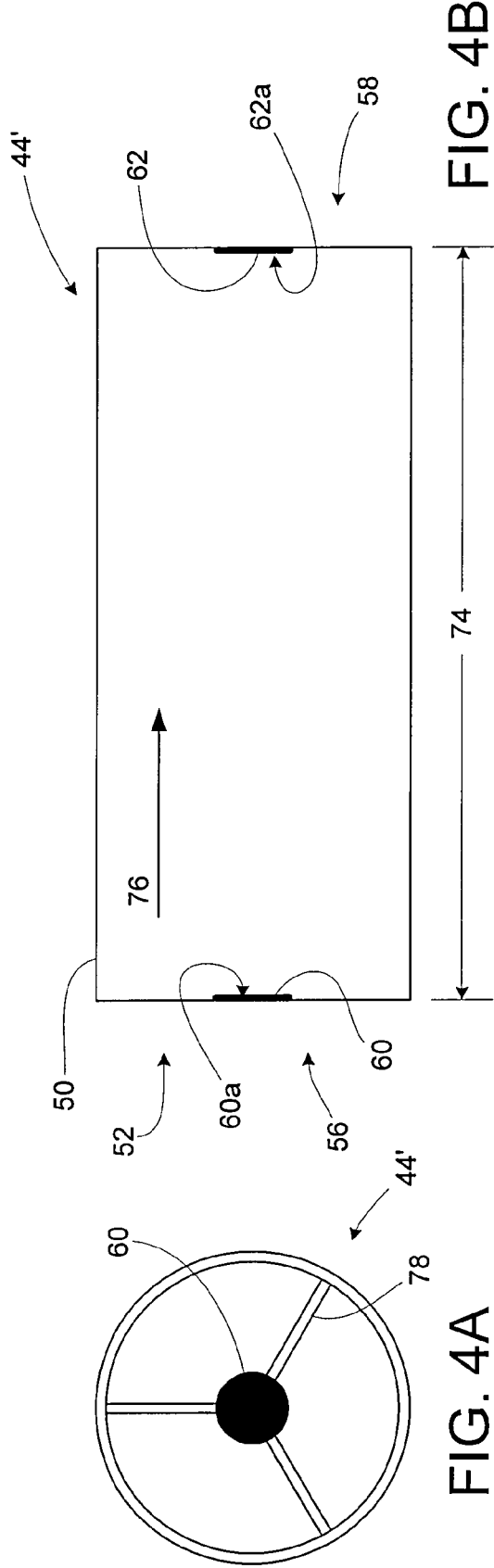
FIG. 4B
FIG. 4A

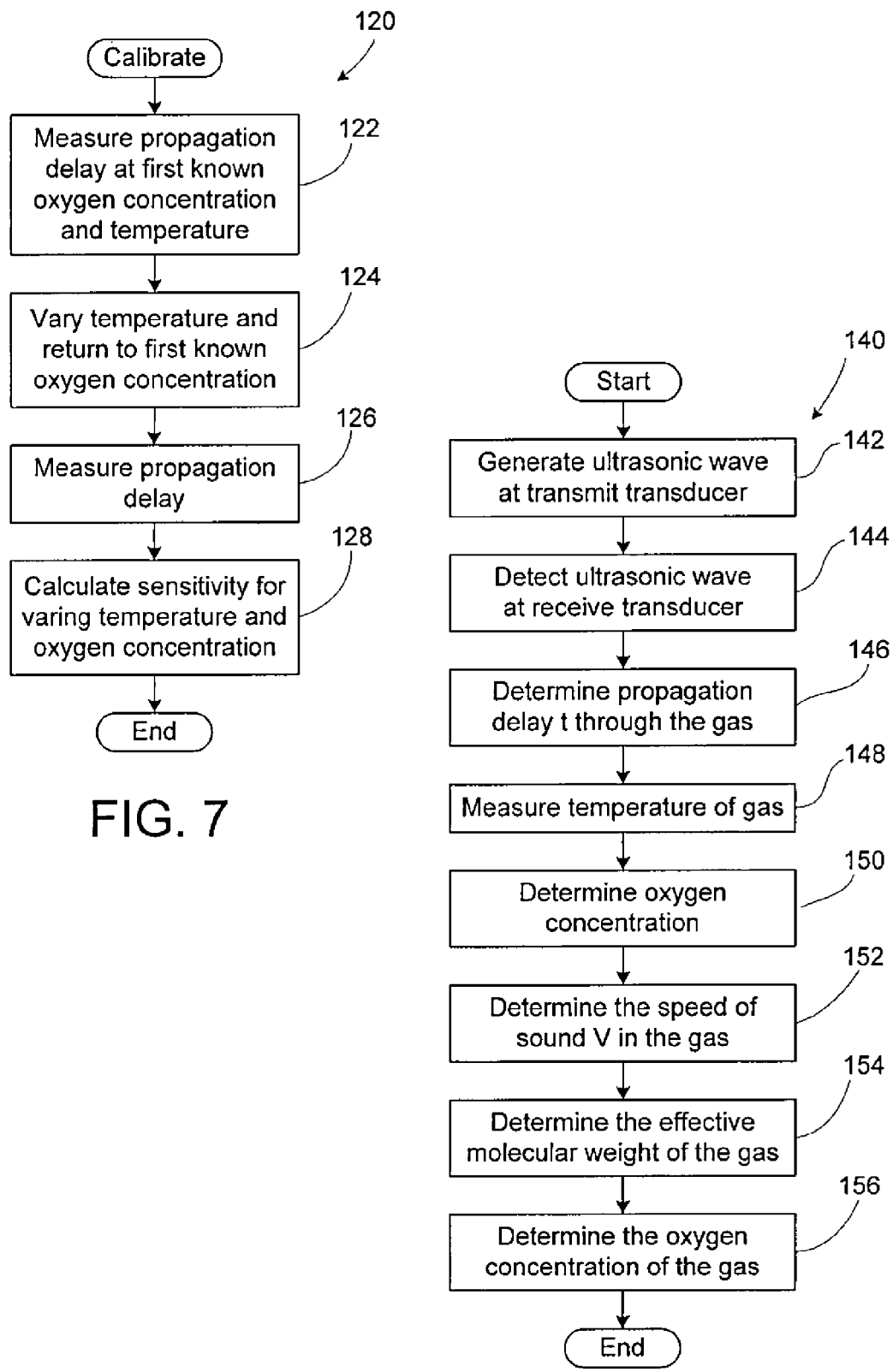

ASM OUTPUT ULTRASONIC OXYGEN SENSOR

FIELD OF THE INVENTION

The present invention relates generally to a gas concentration sensor and, more specifically, to an ultrasonic oxygen concentration sensor for verifying ullage oxygen concentration on an aircraft.

BACKGROUND OF THE INVENTION

Military aircraft have used on-board inert gas generating systems (OBIGGS) for some years to protect against fuel tank explosions due to undesired phenomena, such as penetration from small arms fire. Military aircraft are not the only aircraft that would benefit from OBIGGS. For example, investigations into the cause of recent air disasters have concluded that unknown sources may be responsible for fuel tank ignition and explosion. Subsequently, OBIGGS has been evaluated as a way to protect commercial aircraft against such fuel tank explosions started by unknown ignition sources.

Ullage gas composition (i.e., the air/fuel mixture above the fuel in the fuel tank) consists of many constituents, including air components (oxygen, nitrogen, water vapor, carbon dioxide) and hydrocarbon compounds (fuel vapors). OBIGGS protects against fuel tank explosions by replacing the potentially explosive air/fuel mixture above the fuel in the tanks (the ullage) with an inert gas (usually nitrogen). The nitrogen is generated by separating oxygen from local, ambient air and pumping the inert product into the fuel tanks.

For OBIGGS, a means of verifying ullage oxygen concentration is necessary to verify proper operation. However, it is difficult to reliably measure oxygen concentration in the ullage without compromising safety. This is due in part to the fact that many conventional oxygen sensors operate at elevated temperatures, which could ignite hydrocarbon fumes in the fuel tank.

One approach used to monitor ullage oxygen concentration is to monitor the oxygen concentration at the output of the OBIGGS air separation module (ASM), where nitrogen enriched air (NEA) flows into the ullage at elevated pressure. The gas composition at the ASM output is nearly free of water and fuel vapors and is much easier to measure. U.S. Pat. No. 6,491,739 to Chrome et al. discloses a system that uses a conventional oxygen sensor to monitor ullage oxygen concentration at the ASM output. Oxygen concentration at the ASM output is a direct measure of OBIGGS operation and an indirect indication of the oxygen concentration in the ullage.

SUMMARY OF THE INVENTION

The invention relates to a gas concentration sensor that can ascertain a gas concentration by measuring a propagation delay of a sonic or ultrasonic wave in the gas. The propagation delay can be calculated such that delay contributions from sources other than the gas itself are canceled. These "other sources" can include mechanical and electrical delays in the ultrasonic transducers, variations in the transducer sensitivity due to age, temperature, pressure, etc.

According to one aspect of the invention, there is provided a sonic or ultrasonic gas measuring device for measuring a concentration of a gas of interest, the gas of interest being one component of a gas having at least two different components. The device can include a sonic or ultrasonic transmitter for generating a sonic or ultrasonic wave, a receiver for detecting the sonic or ultrasonic wave, and a reflector positioned to reflect back to the receiver the sonic or ultrasonic wave after having previously been detected by the receiver, whereby a measurement of propagation delay between initially detecting the sonic or ultrasonic wave and subsequently detecting the sonic or ultrasonic wave can be detected.

According to another aspect of the invention, there is provided a method of measuring a concentration of a gas of interest, the gas of interest being one component of a gas having at least two different components. The method can include measuring a propagation delay of an ultrasonic wave as the wave travels through the gas, wherein the propagation delay is measured such that delay contributions from sources other than the gas itself are canceled.

The invention also provides an on-board inert gas generating system (OBIGGS) and an oxygen concentration sensor for determining the oxygen concentration in the ullage. The invention can be used to detect the oxygen concentration in gas exiting the air separation module (ASM) of the OBIGGS. The oxygen concentration of the gas exiting the ASM is a direct measure of OBIGGS operation and an indirect measure of the oxygen concentration in the ullage. When used in OBIGGS, the gas concentration sensor increases the accuracy of the OBIGGS.

According to a further aspect of the invention, there is provided an on-board inert gas generating system for replacing potentially explosive gas in the ullage of an aircraft. The system can include an air separation module (ASM) for generating an inert gas, and an oxygen sensor coupled to the output of the ASM. The oxygen sensor can include a sonic or ultrasonic transmitter for generating a sonic or ultrasonic wave, a receiver for detecting the sonic or ultrasonic wave, and a control unit. The control unit can measure a propagation delay of the sonic or ultrasonic wave between the transmitter and receiver such that the measurement cancels contributions from sources other than the gas itself.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed.

BRIEF DESCRIPTION OF THE DRAWINGS

FIG. 3 is a detailed schematic diagram of the output stage of the OBIGGS system of FIG. 1.

FIG. 4A is a front view of another exemplary oxygen sensor in accordance with the invention.

FIG. 4B is a side view of the oxygen sensor of FIG. 4A.

FIG. 7 is an exemplary flow diagram for calibrating the oxygen concentration sensor in accordance with the invention.

FIG. 8 is another exemplary flow diagram for measuring the oxygen concentration in a gas in accordance with the invention.

DETAILED DESCRIPTION

Figure 1:
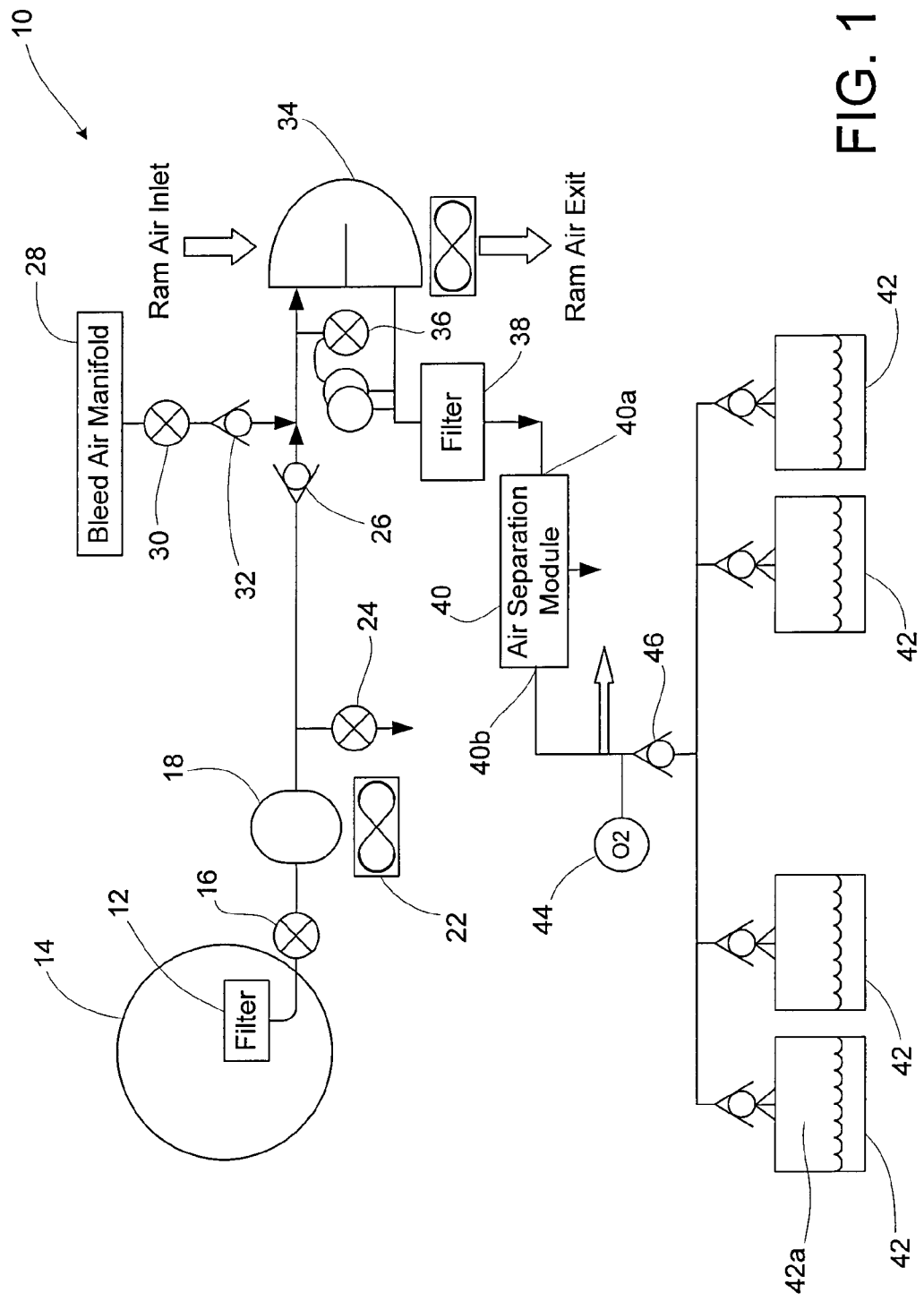
FIG. 1 is an exemplary schematic diagram of an on-board inert gas generating system configuration that can be used with the present invention.

The present invention relates to a sensor for determining the concentration of oxygen within a gas of interest. The oxygen concentration sensor includes a sonic or ultrasonic transmitter (also referred to as a transmit transducer) for generating sonic or ultrasonic waves, and a sonic or ultrasonic receiver (also referred to a receive transducer) for detecting the sonic or ultrasonic waves generated by the transmitter. Further, the oxygen concentration sensor can include other sensors, including one or more temperature sensors, humidity sensors, or sensors for measuring other types of gas. Preferably, the oxygen concentration sensor is cylindrical in shape, although any shape may be used as required by the specific application.

Oxygen concentration is determined based on ultrasonic wave velocity in the gas of interest (hereinafter referred to as "gas") changing with the average molecular weight of the gas. As will be described in more detail below, the sonic or ultrasonic wave velocity or "speed of sound" in the gas is determined by measuring a propagation delay between the transmitter and the receiver.

Preferably, the propagation delay is determined based on a measured time delay between a first and second round trip pulse. The first round-trip pulse is the second received pulse (the first received pulse is the direct propagation delay). The second received pulse is the sonic or ultrasonic wave generated by the sonic or ultrasonic wave reflecting off a face of the receiver, then reflecting off a face of the transmitter and finally being detected by the receiver. This pulse occurs at twice the propagation delay after the first pulse is received. As a result, the measured delay path includes only the gas between transducer faces, and not internal transducer delays. In other words, measurement of the round trip time cancels contributions to the time of flight measurement from sources other than propagation through the gas itself, such as electronic delays, transmission through the transducers, etc. Using the round trip pulse time also has the benefit of eliminating the need to synchronize the recording of the transmit and receive signals.

The propagation delay also can be determined using other methods. For example, the propagation delay can be measured directly, e.g., by measuring the time required for one pulse to travel from the transmitter to the receiver, and compensating the measurement based on temperature variations between the measured delay and a reference delay. Alternatively, the propagation delay can be measured using a continuous wave method with a phase-locked-loop to measure the phase difference between the transmit and receive signals. Such measurement techniques will be described in more detail below.

The present invention now will be described in the context of an on-board inert gas generating system (OBIGGS) used on an aircraft. It will be appreciated, however, that the invention can be applied to various other applications, and the context of measuring oxygen concentration in an OBIGGS is not intended to be limiting in any way. Further, while the invention is described with respect to an oxygen concentration sensor, the invention can be applied to the measurement of other types of gases.

Referring initially to FIG. 1, there is shown an exemplary OBIGGS configuration 10 that can be used in conjunction with the present invention. OBIGGS are well known by those skilled in the art and, therefore, a detailed description of the OBIGGS operation will not be provided herein. Briefly, air is drawn through a filter 12 located in the aircraft cabin 14. The filtered air is routed through a shutoff valve 16 and to a compressor 18. A cooling fan 22 provides cooling air to the compressor 18. After passing through the compressor 18, the compressed and filtered air is routed to an unloading valve 24 and to a temperature sensor 26. Air also can be bled from the system via a bleed air manifold 28, which is routed to a bleed shutoff valve 30 and temperature sensor 32. The compressed/filtered air then is routed to a heat exchanger 34 and a heat exchanger bypass valve 36. The output of the heat exchanger 34 and heat exchanger bypass valve 36 are coupled to a water separator filter 38, which removes water from the cooled air. The cooled air is routed to an air separation module (ASM) 40 having an inlet 40a and outlet 40b. The ASM 40 removes oxygen from the air and provides inert gas to the ullage 42a of fuel tanks 42. An oxygen sensor 44 monitors the oxygen concentration of the inert gas as it leaves the ASM 40. One or more temperature sensors 46 monitor the temperature of the gas exiting the ASM and/or entering the ullage 42a.

As can be seen in FIG. 1, the ASM output 40b is coupled to the ullage 42a and the oxygen sensor 44. Thus, if ASM pressure drops significantly, hydrocarbon enriched ullage air can flow back to the ASM output 40b and oxygen sensor 44. Accordingly, safety considerations that apply to a ullage sensor also apply the ASM output 40b and the oxygen sensor 44. In addition, a check valve (not shown) may be required to prevent ullage fumes from contaminating the ASM 40, the ASM output 40a and/or the oxygen sensor 44.

Figures 2A, 2B:
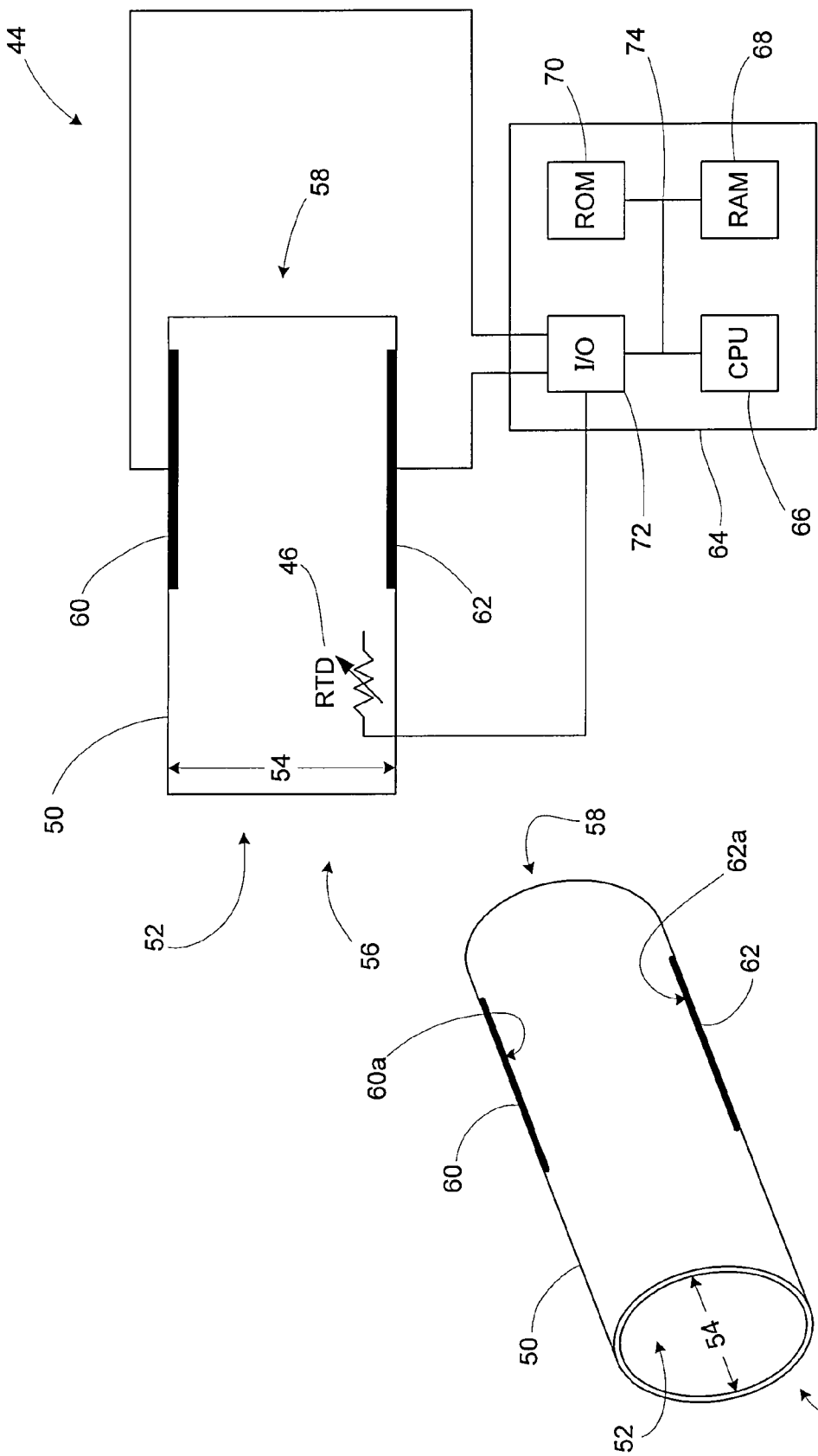
FIG. 2A is a perspective view of an exemplary oxygen concentration sensor in accordance with the invention.
FIG. 2B is a partial schematic view of the oxygen sensor of FIG. 2A.

Referring to FIGS. 2A and 2B, there is shown a simple perspective view and side/partial schematic view of an exemplary oxygen concentration sensor 44 in accordance with the present invention. The sensor 44 includes a housing 50 having a cylindrical chamber 52 therein. The housing can be formed of conventional materials, such as hard plastic or the like. The chamber 52 has a diameter 54 through which the gas can pass, and can be formed from aluminum, for example. While a cylindrical chamber is illustrated, it will be appreciated that other chamber shapes may be employed without departing from the scope of the invention. For example, the chamber may be rectangular, semi-circular, etc. The chamber 52 includes an inlet 56 for receiving the gas and an outlet 58 for exhausting the gas. A transmit transducer 60 for generating sonic or ultrasonic waves is fastened (e.g., bonded) to one side of the chamber 52, and a receive transducer 62 for receiving the sonic or ultrasonic waves is fastened on an opposing side of the chamber 52. The ultrasonic waves generated by the transmit transducer 60 can range from about 20 kHz up to 1 MHz, and preferably are in the range of about 200 kHz. Sonic waves can range between about 5 kHz and 20 kHz. Preferably, the transmit and receive transducers are piezoelectric transducers, although other types of transducers also may be used. A transducer that can be used with the invention is a Polaroid model 200 KHF18 transducer, for example.

A control module 64 (FIG. 2B) is electrically coupled to the transmit and receive transducers 60, 62, and includes circuitry for sending and receiving signals to/from the respective transducers. The control module 64 can include a microprocessor 66, RAM 68, ROM 70, and input/output (I/O) module 72, communicatively coupled via a system buss 74, as is conventional. The control module 64 can transmit and receive signals from the transducers 60, 62, one or more temperature sensors 46, or other devices (e.g., a humidity sensor 75—FIG. 3) via the I/O module 72. Further, the one or more temperature sensors 46 and/or other devices may be integrally included with the oxygen sensor 44 or separate from it.

The control module 64 is configured to command the transmit transducer 60 to generate a sonic or ultrasonic wave, and to receive from the receive transducer 62 a signal corresponding to detection of the sonic or ultrasonic wave. Preferably, the control module 64 is configured to command the transmit transducer 60 to generate pulsed sonic or ultrasonic waves (as opposed to continuous waves). Pulsed waves will not produce standing waves that create spurious reflections that can degrade the measurement. As will be described in more detail below, the control module 64 ascertains the oxygen concentration within the gas passing through the chamber 52 based on the speed of sound in the gas, the temperature of the gas, and the molecular weight of the gas. The control module 64 can be located remote from the oxygen sensor 44 (e.g., physically separated from the sensor) or located local to the oxygen sensor 44 (e.g., on or in the sensor).

Since the ASM output gas is relatively clean, the oxygen concentration of the output gas can be determined by measuring the speed of sound through the gas, which is a function of the average or effective molecular weight of the gas components. It is assumed that only nitrogen and oxygen gas concentrations will vary at the ASM output 40b. If other gas concentrations (such as water vapor or hydrocarbons) also vary, additional gas sensors (e.g., the humidity sensor 75) may be needed to measure for such gasses and to correct for their variations. Further, it is assumed that ambient air (unenriched) can be used as a calibration reference at 20.8% oxygen (provided the ambient air is dried and well filtered).

With further reference to FIG. 3, a schematic diagram illustrating in more detail the configuration of the OBIGGS output stage. Specifically, the output of the ASM 40 is coupled to the above-described oxygen concentration sensor 44 and temperature sensor 46. Nitrogen enriched air (NEA) exiting the ASM 40 passes through the oxygen sensor 44 and is injected into the fuel tank 42. As the NEA passes through the oxygen sensor 44, sonic or ultrasonic waves are transmitted from the transmit transducer 60 to the receive transducer 62, and the temperature of the NEA is measured by the temperature sensor 46. The sonic/ultrasonic and temperature data is communicated to the control module 64 and, based on the collected data, a calculation of the oxygen concentration of the NEA is provided, as described in more detail below.

Since the speed of sound is sensitive to temperature as well as to the gas medium, the temperature sensor 46 monitoring the ASM output should be a high accuracy temperature sensor (e.g., accuracy within 0.1 degrees C. or better). As discussed below, a small change in gas temperature could mask a change in oxygen concentration. As a result, a change in temperature relative to the air calibration temperature should be measured precisely. Absolute temperature accuracy, however, is not that important.

The speed of sound V (m/sec) can be measured by placing two transducers across an output pipe of the ASM at a fixed, known distance s (meters). Such a configuration is provided in the oxygen sensor 44 described in FIGS. 2A and 2B, wherein transmit and receive transducers 60, 62 are separated by the diameter 54 (the distance s) of the chamber 52. The time delay t (seconds) between transmitting a pulse from the transmit transducer 60 and receiving the pulse at the receive transducer 62 can be measured and V can be calculated using Equation 1.

$$V = \frac{s}{t} \quad \text{Equation 1}$$

The speed of sound through a gas is a function of its effective molecular weight and the temperature of the gas. Equation 2 below defines the speed of sound in gas, where V is the speed of sound in the gas in meters per second, $\delta$ is the adiabatic gas constant for the gas (approximately 1.4 for air), R is the universal gas constant, T is absolute temperature (degrees Kelvin) and $\phi_e$ is the effective molecular weight (weighted average of component gases MW). Equation 3 is Equation 2 rewritten to solve for $\phi_e$.

$$V = \sqrt{\frac{\delta RT}{\phi_e}} \quad \text{Equation 2}$$

$$\phi_e = \frac{\delta RT}{V^2} \quad \text{Equation 3}$$

If the gas consists of only the two variable components, nitrogen and oxygen (assuming trace gases such as argon and carbon dioxide are at constant concentrations), the oxygen concentration is a function of the effective molecular weight and the molecular weights of oxygen and nitrogen, as defined in Equation 4, where $C_O$ is the oxygen concentration in percent, $\phi_e$ is the effective molecular weight (calculated from the speed of sound in Equation 3), $\phi_O$ is the molecular weight of oxygen (32 for $O_2$) and $\phi_n$ is the molecular weight of nitrogen (28 for $N_2$).

$$C_O = \frac{\phi_e - \phi_n}{\phi_O - \phi_n} * 100 \quad \text{Equation 4}$$

Accordingly, the oxygen concentration of the gas can be quickly and easily calculated by measuring the temperature and propagation delay of the sonic or ultrasonic wave across the two transducers while the gas passes between the transducers.

To maintain a high rate of accuracy, the system can be calibrated using non-enriched air, where $C_O$ is about 20.8%. This allows the system to calibrate out any fixed propagation delay sources, such as electronic delays, cable length delays, etc. Once the system is calibrated at a known oxygen concentration, a change in measured propagation delay relative to the reference delay indicates a change in oxygen concentration (after temperature correction).

For example, assuming that the chamber 52 has a diameter 54 of 1.0 inch, then the transducer separation would be 1.0 inch. At room temperature (25 degrees C.) and normal air concentration ($C_O$=20.8%), $V_{air}$ is 331.45 m/sec (13,049.2 in/sec). In this configuration, the propagation delay t across a 1.0 inch path would be 76.633 μsec, and $\phi_e$ would be 28.842.

For a 1% drop in oxygen concentration ($C_O$=19.8%) at constant temperature, $\phi_e$ is 28.802 and $V_{air}$ is 331.68 m/sec (13,058.3 in/sec) (note that in Equation 2 V is inversely proportional to the square root of $\phi_e$). As a result, the propagation delay t across a 1.0 inch path would be 76.580 μsec and the change in propagation delay $\Delta t_{inch}$ for a 1.0 inch acoustic path would be 53 nsec. This results in a sensitivity of 53 nsec for a 1% change in concentration.

If the oxygen concentration is further reduced ($C_O$=0.8% at constant temperature), $\phi_e$ is 28.045 and $V_{air}$ is 336.13 m/sec (13,233.3 in/sec). The propagation delay t across a 1.0 inch path would be 75.567 μsec and the change in propagation delay $\Delta t_{1inch}$ for a 1.0 inch acoustic path would be 1.066 μsec. This again corresponds to a sensitivity of $\Delta t_{1inch}$=53 nsec for a 1% change in $C_O$. Thus, the sensitivity is linear over the operation range of the sensor.

To resolve $C_O$ to 1%, the propagation delay measurements should be resolved to about 50 nsec for a 1.0 inch acoustic path. It is noted that the sensitivity of 53 nsec per 1% $C_O$ change is linear and, therefore, doubling the path length to 2.0 inches doubles the output to $\Delta t_{2inch}$=106 nsec per 1% change in $C_O$.

From Equation 2, it can be seen that V is proportional to the square root of temperature (T). If, for example, the ASM gas temperature rises from 25 degrees C. to 35 degrees C. with $C_O$ constant at 20.8%, then $V_{air}$ is 336.97 m/sec (13,266.4 in/sec), and the propagation delay t across a 1.0 inch path would be 75.379 μsec, resulting in a change in propagation delay $\Delta t_{1inch}$ for a 1.0 inch acoustic path of 1.254 μsec. This corresponds to a propagation delay sensitivity of $\Delta t_{1degC}$=125.4 nsec per degree C. The temperature sensitivity of 125.4 nsec per 1 degree C. also is linear over the operating range of the sensor. Further, gas temperature should be measured with high precision, as a temperature change of 0.1 degrees C. can mask a $C_O$ change of 0.24%.

The most straightforward approach to measuring the propagation delay is to use a pulsed transmit method, where only one or a small number of cycles at the transducers' resonant frequency are transmitted via the transmit transducer. Since the efficiency of air-coupled transducers is low, it is advantageous to transmit at the transducers' resonant frequency, as transmitting off resonance further reduces the amplitude of the signal. The receive transducer 62 sees the time shifted signal and the transmit to receive time can be determined. If the propagation delay is measured by digitizing the analog waveform from the receive transducer 62 and the time shift of the waveform relative to the calibration position is measured (at a known oxygen concentration of 20.8% for air), an ADC sampling rate of approximately 80 MHz (for a 12.5 nsec time resolution, corresponding to 0.25% $C_O$ resolution) should be used if the acoustic path is 1.0 inch. The sampling speed can be lowered if the acoustic path is increased.

If using an ADC, the easiest approach for determining change in propagation delay is to apply a cross-correlation algorithm to the received signal waveform relative to the stored reference waveform (at a known temperature and $C_O$). This calculation can be done using either a low end digital signal processor (DSP) or a general-purpose microcontroller.

Alternatively, the need for a reference waveform can be avoided by performing an auto-correlation on the received signal waveform and measuring the time between the first received pulse and the second received pulse (the first round trip reflection). This measurement is twice the propagation delay between the two transducer faces and eliminates any internal transducer delays (and their variability). To further enhance accuracy, the entire received waveform (including multiple round trip pulses) can be digitized, and a windowed cross-correlation technique can be used to accurately determine the time delay between the first (direct) and second (round trip) pulses. Using this technique, time delay errors can be less than the ADC sampling time interval. Further, delays relating to commanding the transmit transducer to generate a sonic or ultrasonic wave, the transmit transducer actually generating a sonic or ultrasonic wave, and the receive transducer detecting the sonic or ultrasonic wave, as well as electrical delays, are effectively eliminated.

Another measurement approach would be to use a continuous wave (CW) method with a phase locked loop (PLL) (not shown) to measure the phase difference between the transmit signal and the received signal. The PLL output error voltage (filtered) is a measure of phase difference and can be digitized with a much slower ADC (any sampling rate well below the transducers resonant frequency, i.e., <<100 kHz). The disadvantage with this approach is it requires the full, worst-case dynamic range of propagation delay, or phase shift (from min T and max $C_O$ to max T and min $C_O$) to fit within ±90 degrees of the transducer's resonant frequency. For 100 kHz transducers, this would be a variation in propagation delay of ±2.5 μsec. In addition, the transmit frequency must be extremely stable. Otherwise a transmit frequency shift will appear as an output phase shift, even at constant T and $C_O$.

Regardless of the exact measurement technique, if the transducer pair is mounted so that the acoustic path has a component parallel to the gas flow direction (parallel to the pipe), the sensor can be used to measure both oxygen concentration and gas flow rate. FIGS. 4A and 4B illustrate an exemplary sensor 44' wherein the transmit and receive transducers 60, 62 are mounted so the acoustic path has a component parallel to the gas flow 76. The transducers are held in the flow path via support members 78, which extend from the housing 50 to the respective transducers 60, 62.

As can be seen in FIG. 4B, the separation s between the transducers 60, 62 is the length 74 of the chamber (as opposed to the diameter 54 of the chamber in the embodiment of FIGS. 2A and 2B). By alternately switching the transmit and receive functions between the two transducers 60, 62, the difference in measured velocity (upstream vs. downstream) is a function of gas flow rate. Further, the average of the two measurements can be used to determine oxygen concentration, as above. This is extremely useful for ASM output applications where both the oxygen concentration and the gas flow rate must be known in order to determine the functionality of the system.

Figure 5:
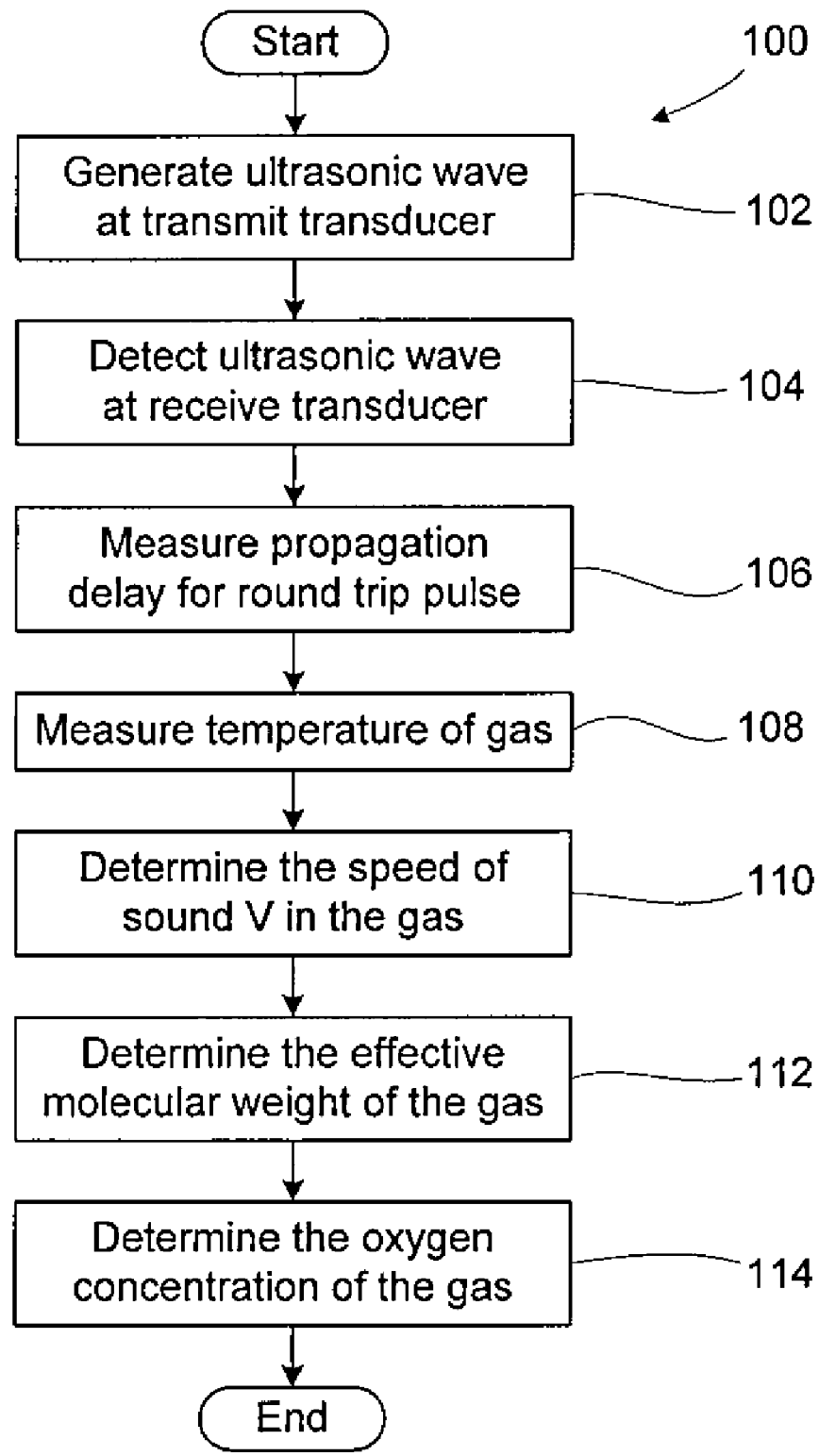
FIG. 5 is an exemplary flow diagram illustrating the steps for measuring oxygen concentration in a gas in accordance with the invention.

Moving now to FIG. 5, a flow diagram 100 illustrating a method of determining the oxygen concentration in a gas in accordance with an embodiment of the invention is shown. The flow diagram includes a number of process blocks arranged in a particular order. As should be appreciated, many alternatives and equivalents to the illustrated steps may exist and such alternatives and equivalents are intended to fall with the scope of the claims appended hereto. Alternatives may involve carrying out additional steps or actions not specifically recited and/or shown, carrying out steps or actions in a different order from that recited and/or shown, and/or omitting recited and/or shown steps. Alternatives also include carrying out steps or actions concurrently or with partial concurrence.

Beginning at step 102, the control module 64 commands the transmit transducer 60 to generate a sonic or ultrasonic wave, which travels through the gas and reaches the receive transducer 62. At step 104, the receive transducer detects the sonic or ultrasonic wave and reports the reception to the control module 64. For example, the receive transducer can simply communicate that the wave has been detected, or the entire waveform (including multiple round trip pulses) can be recorded by the control module 64.

Figure 6:
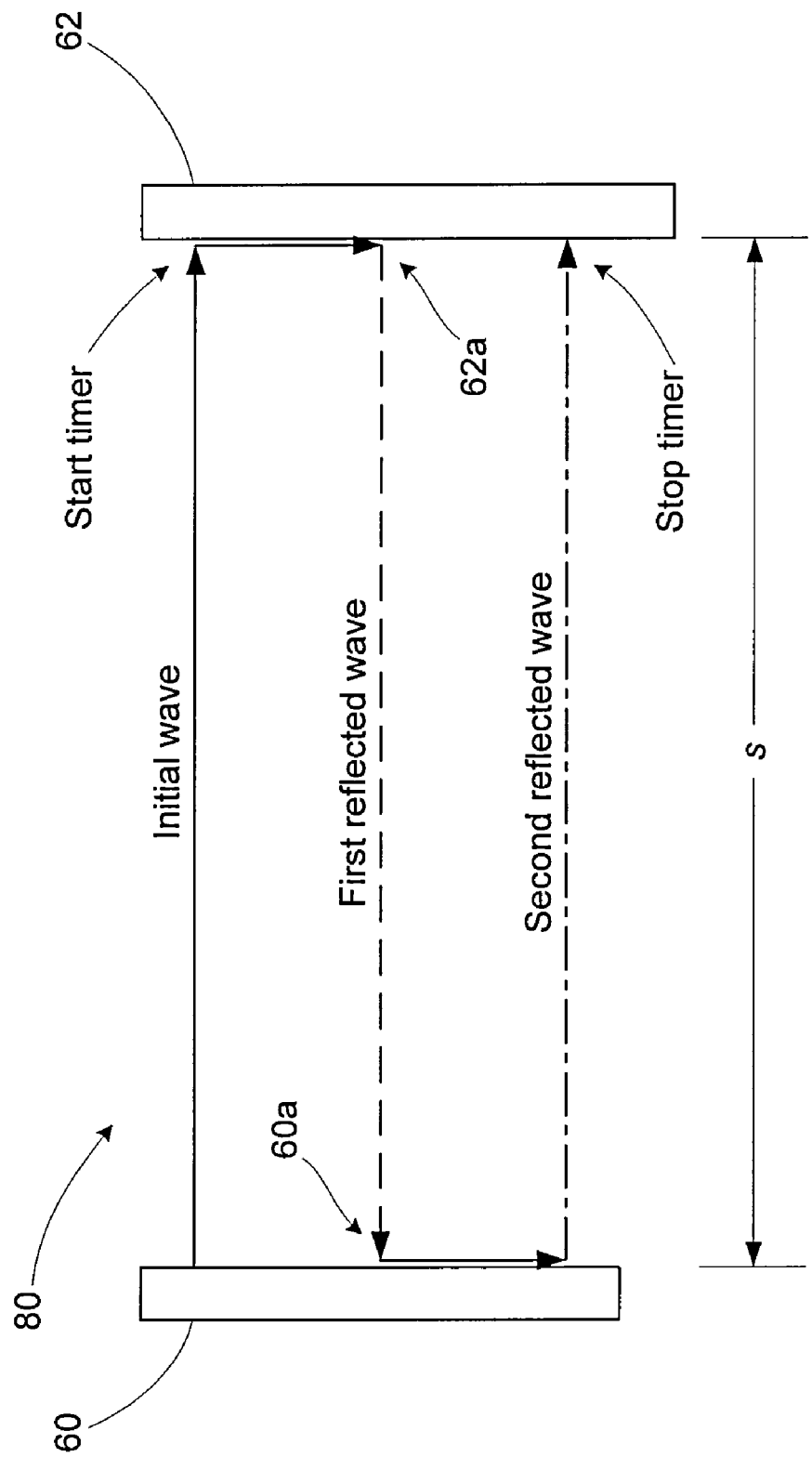
FIG. 6 is a schematic diagram illustrating the sound waves traveling between the transmit transducer and the receive transducer.

Next, at step 106 the control module 64 calculates the propagation delay of the sonic or ultrasonic wave through the gas. With further reference to FIG. 6, as the sonic or ultrasonic wave 80 is detected by the receive transducer 62, a timer (not shown) begins timing. The sonic or ultrasonic wave, after striking the face 62a (e.g., a first reflector) of the receive transducer 62, bounces off the receive transducer and travels back to the transmit transducer 60. When the wave strikes the face 60a (e.g., a second reflector) of the transmit transducer, it bounces off the transmit transducer and travels back to the receive transducer 62. Now, when the wave is again detected by the receive transducer 62, the timer is stopped and the value in the timer is the time for the sonic or ultrasonic wave 80 to travel twice the distance of separation (2s). Moreover, since the timer is not started until the receive transducer has detected the wave, delays associated with commanding the transmit transducer 60 to generate the sonic or ultrasonic wave and mechanical delays associated with the transmit transducer 60 generating the sonic or ultrasonic wave are eliminated. Further, the distance the wave travels through the gas is doubled (i.e., 2s), thereby allowing a larger data sample to be collected. These factors result in enhanced accuracy of the propagation delay and, therefore, enhanced accuracy of the calculations performed by the sensor 44.

Alternatively, instead of using a timer, the entire wave form received by the receive transducer 62 can be digitized (including multiple round trip pulses), and a windowed cross-correlation technique can be used to accurately determine the time delay between the first (direct) and second (round trip) pulses. This technique can reduce the time delay error to less than the ADC sampling time interval (normally ten nanoseconds).

The temperature of the gas is measured at step 108, and at step 110, the speed of sound V in the gas is determined using Equation 1, for example. More specifically, the separation s (meters) of the transmit and receive transducers 60, 62 is known, while the propagation delay t (i.e., the time in seconds required for the sonic or ultrasonic wave to travel the distance s) was determined in step 106 above. The speed of sound V through the gas is the distance of separation divided by the time t required to traverse the distance s.

Next, at step 112, the effective molecular weight $\phi_e$ of the gas is determined from Equation 3. More specifically, the speed of sound V in the gas derived in step 110 and the measured temperature T of the gas from step 108 are used along with the adiabatic gas constant $\delta$ and the universal gas constant R to determine the effective molecular weight of the gas. Once the effective molecular weight $\phi_e$ of the gas has been determined, it is used in conjunction with the known molecular weights of oxygen and nitrogen in Equation 4 to determine the oxygen concentration $C_O$ within the gas, as indicated at step 114.

Moving now to FIGS. 7 and 8, exemplary flow charts 120 and 140 are shown which correspond to method in accordance with another embodiment for determining the oxygen concentration. FIG. 7 corresponds to a calibration procedure, while FIG. 8 corresponds to the actual oxygen concentration measurement.

Beginning with step 122, the propagation delay of the sonic or ultrasonic wave is measured from the transmit transducer 60 to the receive transducer 62. This measurement is performed at a known oxygen concentration (e.g., 20.8%) and at a known temperature (e.g., 25 degrees C.).

Moving to step 124, the temperature of the gas is varied to a known level different from the temperature in step 122 while maintaining the oxygen concentration. At step 126, the propagation delay from the transmit transducer 60 to the receive transducer 62 is measured.

The collected data is assembled and the temperature sensitivity of the sensor is determined at step 128. More specifically, the temperature sensitivity can be determined by calculating the change in propagation delay for a 1 degree C. temperature change. For example, if the propagation delay at the first temperature (25 degrees C.) was calculated at 76.633 µsec, and the propagation delay for the second temperature (35 degrees C.) is 75.379 µsec, then the sensitivity can be determined by the change in propagation delay divided by the change in temperature (e.g., 1.254 µsec divided by 10 degrees C.), which results in a sensitivity of 125.4 nsec per 1 degree C. change in temperature. This value is stored in memory for later use.

Moving now to the flow chart of FIG. 8, measurement of the oxygen concentration in accordance with the alternative embodiment will be described. Beginning at step 142, the control module 64 commands the transmit transducer 60 to generate a sonic or ultrasonic wave, which travels through the gas and reaches the receive transducer 62. At step 144, the receive transducer detects the sonic or ultrasonic wave and reports the reception to the control module 64.

Next, at step 146 the control module 64 calculates the propagation delay of the sonic or ultrasonic wave through the gas. The propagation delay can be calculated using a conventional method, e.g., measuring the time delay between initiating the sonic or ultrasonic wave at the transmit transducer 60 and receiving the wave at the receive transducer 62. At step 148, the temperature of the gas is measured.

Moving to step 150, the measured propagation delay is temperature compensated using the correction value obtained during calibration (FIG. 7). More specifically, the propagation delay is corrected for temperature using Equation 5 below, where $t_{comp}$ is the compensated propagation delay in seconds, $t_{meas}$ is the measure propagation delay in seconds, $T_1$ is the measured temperature in degrees C, T is the calibration temperature in degrees C (e.g., 25 degrees C.) and $t_{sensitivity}$ is the temperature sensitivity obtained during calibration of the sensor in seconds per degree C. Equation 5 is valid for ideal systems having transducer spacings that do not vary with temperature.

$$t_{comp} = t_{meas} + (T_1 - T) * t_{sensitivity} \quad \text{Equation 5}$$

Once the temperature compensated propagation delay $t_{comp}$ is determined, the oxygen concentration can be determined in the same manner described in steps 110-114 of FIG. 5, wherein steps 152, 154 and 156 correspond to steps 110, 112 and 114, respectively. Accordingly, discussion of these steps are omitted for sake of brevity.

The accuracy of the sensor 44 can be further enhanced by utilizing a "high fidelity" model within the sensor. For example, the sensor can include an enhanced mathematical model of the system, including corrections for non-ideal gas behavior (pressure dependency) and variations in adiabatic gas constant ($\delta$) with both temperature and gas concentration. Further, thermal drift of the transmit to receive transducer separation also can be taken into account. The use of a "high fidelity" model can improve accuracy from the 1-2% range to approximately the 0.25-0.5% range. An exemplary high fidelity model is discussed below.

Adiabatic Gas Constant Corrections

In the simplified model based on Equations 2 and 3, the adiabatic gas constant $\delta$ was assumed to be constant. In practice, however, $\delta$ varies with gas concentration and temperature (i.e., $\delta = f(C_O, T)$). The adiabatic gas constant $\delta$ is the ratio of specific heats for that gas ($\delta = C_p/C_v$).

For a mixture of oxygen and nitrogen, $\delta_{mix}$ is a function of the individual gas heat capacities, as shown in Equation 6.

$$\delta_{mix} = \frac{\frac{C_{O2}}{100} \times (Cp_{O2} - Cp_{N2})}{\frac{C_{O2}}{100} \times (Cp_{O2} - Cp_{N2}) + Cp_{N2} - R} \quad \text{Equation 6}$$

where $C_{O2}$ is the oxygen concentration, $Cp_{O2}$ is the oxygen heat capacity, $Cp_{N2}$ is the nitrogen heat capacity and R is the universal gas constant.

Since the heat capacities vary with temperature, $\delta_{mix}$ also is a function of temperature. Typically, $Cp_{O2}$ and $Cp_{N2}$ are fit into polynomials and then used in Equation 6. Since a value of $C_{O2}$ is needed to calculate $\delta_{mix}$, an iterative process is used to first use an approximate value of $\delta_{mix}$ to calculate an approximate $C_{O2}$ and then continue looping with new values of $\delta_{mix}$ and $C_{O2}$ until the $C_{O2}$ value converges.

Non-Ideal Gas Corrections

Equations 2 and 3 assume ideal gas behavior. The properties of real gases, however, vary both with temperature and pressure. For example, the compressibility factor Z of a real gas deviates from 1.0 when environmental conditions vary from Standard Temperature and Pressure. Equation 3 can be rewritten as shown in Equation 7 below.

$$\phi_e = \frac{\delta_{mix} \times R \times T * \left[ \frac{Z_{mix}}{1 - \frac{P}{Z_{mix}} \times \left( \frac{\Delta Z_{mix}}{\Delta P} \right)_T} \right]}{V^2} \quad \text{Equation 7}$$

The gas correction term of Equation 7 (in brackets) corrects for pressure-dependent gas behavior, where P is the gas pressure, $Z_{mix}$ is the compressibility of the gas mixture and can be expressed by the function $f(P,T, C_{O2})$. $(\Delta Z_{mix}/\Delta P)_T$ is the change in gas mixture compressibility with change in pressure at constant temperature.

The above described methodology can be implemented by a computer program which, when it is loaded onto a computer or is running on a computer (e.g., the control module 64), performs one or more of the method steps described above. The program can be embodied in a program storage medium, such as ROM, PROM, EEPROM, flash RAM, magnetic tape or disk, optical disk, or the like, as is conventional.

Accordingly, an apparatus and method for determining the oxygen concentration within a gas has been disclosed. The invention provides increased accuracy relative to prior art oxygen sensors using a "high fidelity" model, and can be used to enhance the accuracy and/or safety of various systems, such as OBIGGS, for example.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A gas measuring device for measuring a concentration of a gas of interest, the gas of interest being one component of a gas having at least two different components, comprising:
   a transmitter for generating a sonic or ultrasonic wave;
   a receiver for detecting the sonic or ultrasonic wave;
   a reflector positioned to reflect back to the receiver the sonic or ultrasonic wave after having previously been detected by the receiver; and
   a processor operatively coupled to the transmitter and receiver, said processor operative to measure a propagation delay between initially detecting the sonic or ultrasonic wave and subsequently detecting the reflected sonic or ultrasonic wave is detected.

2. The gas measuring device of claim 1, wherein the gas concentration is determined based on sonic or ultrasonic wave velocity in the gas changing with the average molecular weight of the gas.

3. The gas measuring device of claim 1, wherein the gas concentration is determined based on a velocity of the sonic or ultrasonic wave through the gas, the temperature of the gas, and the molecular weight of the gas.

4. The gas measuring device of claim 1, further comprising a control module operatively configured to apply a cross-correlation algorithm to the received signal waveform.

5. The gas measuring device of claim 1, wherein the propagation delay is based on a measured time delay of a round trip pulse of the wave after the first detection.

6. The gas measuring device of claim 5, wherein the round trip pulse includes a first received pulse and a second received pulse.

7. The gas measuring device of claim 5, wherein the round trip pulse is generated from the wave reflecting off a face of the receiver, then reflecting off a face of the transmitter and arriving back at the receiver.

8. The gas measuring device of claim 7, wherein the entire received waveform is recorded.

9. The gas measuring device of claim 1, wherein the propagation delay is measured as the time of flight of the wave between the transmit and receive transducers, and the measurement is compensated based on temperature.

10. The gas measuring device of claim 1, wherein the propagation delay is measured using a phase difference between the transmitted wave and the received wave.

11. The gas measuring device of claim 1, wherein the transmitter generates pulsed waves.

12. The gas measuring device of claim 11, wherein the pulsed waves are transmitted at the transmitter and receiver resonant frequency.

13. The gas measuring device of claim 1, further comprising at least one temperature sensor for measuring a temperature of the gas passing through the device.

14. The gas measuring device of claim 1, wherein the transmitter and receiver are piezoelectric transducers.

15. The gas measuring device of claim 1, wherein the transmitter and receiver are mounted so that an acoustic path of the wave has a component parallel to a gas flow direction.

16. The gas measuring device of claim 1, further comprising a control unit operatively configured to determine the concentration of the gas based on a high-fidelity model, wherein the high-fidelity model includes corrections for at least one of non-ideal gasses or an adiabatic gas constant.

17. A gas measuring device for measuring a concentration of a gas of interest, the gas of interest being one component of a gas having at least two different components, comprising:
   a housing including an inlet for receiving the gas and an outlet for exhausting the gas;
   a transmitter for generating a sonic or ultrasonic wave;
   a receiver for detecting the sonic or ultrasonic wave;
   a reflector positioned to reflect back to the receiver the sonic or ultrasonic wave after having previously been detected by the receiver,
   wherein said transmitter and receiver are fastened to the housing opposite one another, and
   whereby a measurement of a propagation delay between initially detecting the sonic or ultrasonic wave and subsequently detecting the reflected sonic or ultrasonic wave is detected.

18. The device according to claim 17, further comprising circuitry operatively coupled to the transmitter and receiver, said circuitry operative to measure the propagation delay.

* * * * *